United States Patent [19]

Pace

[11] 4,085,009
[45] Apr. 18, 1978

[54] METHODS FOR DETERMINATION OF ENZYME REACTIONS

[75] Inventor: Salvatore J. Pace, Yorktown Heights, N.Y.

[73] Assignee: Technicon Instruments Corporation, Tarrytown, N.Y.

[21] Appl. No.: 709,470

[22] Filed: Jul. 28, 1976

[51] Int. Cl.² ............................................. G01N 27/46
[52] U.S. Cl. .................. 204/1 T; 204/195 B; 195/103.5 R
[58] Field of Search ............... 204/1 E, 195 B, 195 P; 195/103.5 R, 103.5 C

[56] References Cited

U.S. PATENT DOCUMENTS

| 3,242,064 | 3/1966 | Byrne | 204/196 |
|---|---|---|---|
| 3,654,116 | 4/1972 | Inoue | 204/129.43 |
| 3,765,841 | 10/1973 | Paulson | 204/1 E |
| 3,838,034 | 9/1974 | Groves | 204/195 P |
| 3,857,771 | 12/1974 | Sternberg | 204/195 P |
| 4,016,044 | 4/1977 | Fresnel et al. | 204/1 E |
| 4,045,297 | 8/1977 | Weeks et al. | 195/103.5 R |

OTHER PUBLICATIONS

Thomas et al., "Analytica Chemica Acta", vol. 78, 1975, pp. 271-276.

*Primary Examiner*—T. Tung
*Attorney, Agent, or Firm*—S. P. Tedesco

[57] ABSTRACT

A method, for microcoulometric determination either of the activity of an enzyme in a liquid sample or the concentration of a substrate for a reaction involving a change in a coenzyme from a first form thereof to a second form. At intervals during the reaction, both coenzyme forms are measured essentially simultaneously utilizing an electrolytic cell, to indicate either such enzyme activity or substrate concentration, depending upon which is the unknown factor.

11 Claims, 4 Drawing Figures

METHODS FOR DETERMINATION OF ENZYME REACTIONS

This invention relates to the coulometric determination of the activity of enzymes in the presence of coenzymes, and particularly kinetic measurements of such enzyme activity.

It is known, as evidenced by L. C. Thomas and G. D. Christian in Voltammetric Measurement of Reduced Nicotinamide-Ademine Nucleotides and Application to Amperometric Measurements of Enzyme Reactions, Analytica Chimica Acta 78(1975)271–276, Elsevier Scientific Publishing Co., Amsterdam, Printed in the Netherlands, that there is a direct relationship in the level of activity of an enzyme LDH (lactate dehydrogenase) in a reaction and a fixed-time change in a coenzyme (NADH) oxidation current resulting from the reaction. In that procedure, a constant voltage was applied continuously to the auxiliary and reference electrodes of a three-electrode patentiostat, and the coenzyme NADH was depleted by the electrochemical reaction at the polarized indicator electrode, i.e., by the conversion of NADH to NAD.

I have found that once the enzyme reaction has been initiated, either solely by the chemical reactants and coenzyme form present or by applying a voltage to produce the necessary oxidized or reduced form of the coenzyme to enable the reaction to proceed, the auxiliary electrode may be pulsed at relatively close intervals from a rest potential to effect current responses of the indicator electrode to both the oxidized and reduced forms of the coenzyme (showing the depletion of one form and the increase in the other form) so as to indicate corresponding enzyme activity at those intervals without disturbing the rate at which the reaction proceeds in one direction and with essentially no conversion of the coenzyme form through such pulsing. This was an unexpected result.

Accordingly, one object of the invention is to provide an improved method for kinetic microcoulometric determination of the activity of enzymes in the presence of coenzymes. Further, when the enzyme level in the presence of a coenzyme form is known, the invention may be utilized to determine the concentration of a substrate present through depletion and formation of the relevant forms of the coenzyme. Another object is to provide a three-electrode potentiostat for simultaneous contact of the electrodes thereof with the solution, the electrodes comprising an auxiliary electrode and an indicator electrode, a device to pulse the auxiliary electrode and measuring both of the coenzyme forms during the reaction as a function of current passing between the auxiliary and indicator electrodes.

Figure 1:
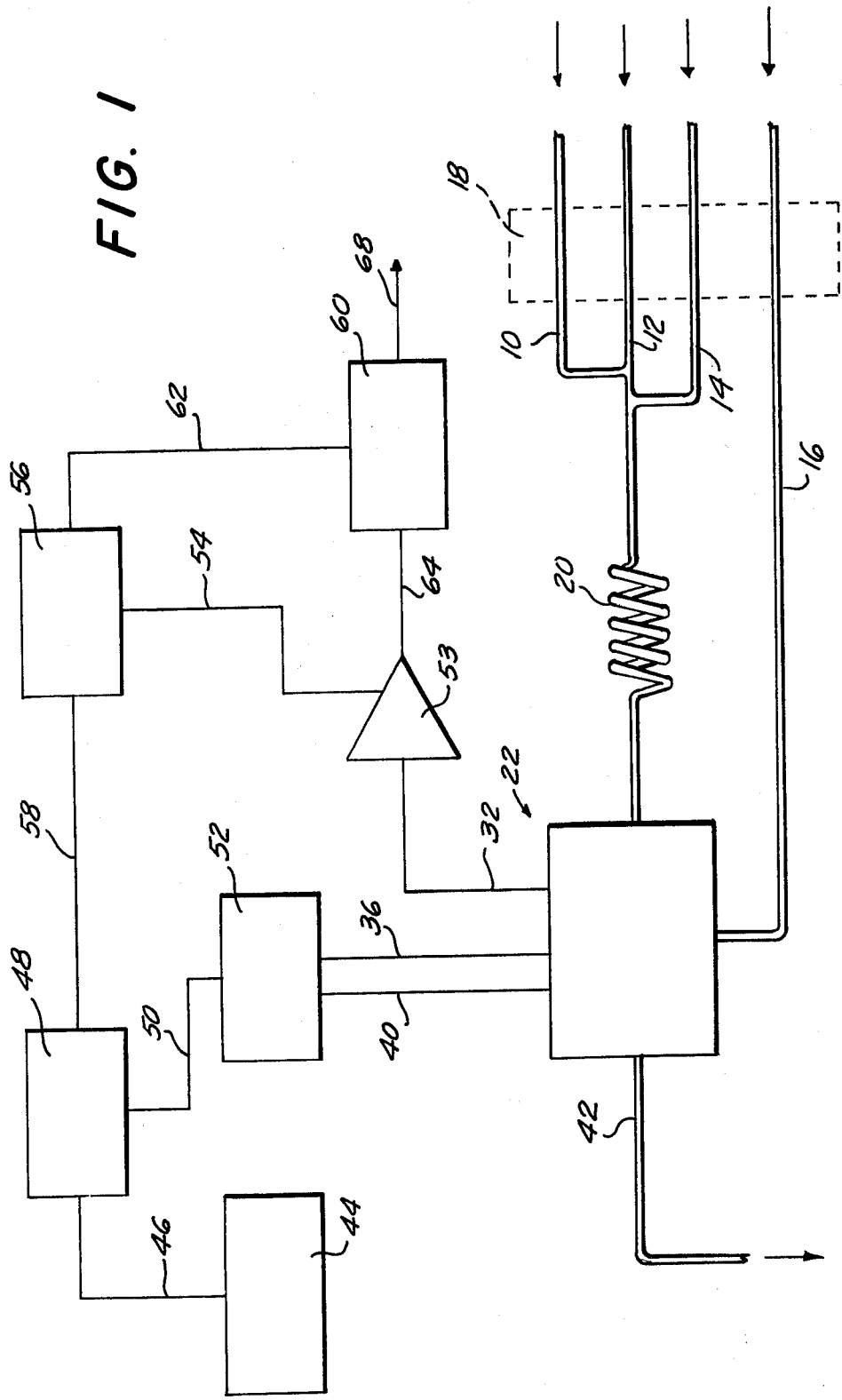
FIG. 1 is a schematic view of apparatus, embodying the invention, for coulometric determination of the activity of enzymes in solution in liquid samples and in the presence of coenzymes.

In FIG. 1, compressible pump tubes 10, 12, 14 and 16 are shown extending through a peristaltic pump 18, the direction of flow in the tubes being indicated by arrows and the tubes 10, 12, 14 having the indicated connections one to another downstream from the pump. In the kinetic determination of the activity of the enzyme LDH, for example, the inlet ends of tubes 10, 12 and 14 maybe supplied with ambient air, pyruvic acid (substrate) in a buffered solution of Tris-Hydroxymethylamine together with NADH (coenzyme), and a liquid sample such as blood serum containing an unknown level of LDH, respectively. The aforementioned fluid substances inputted through the tubes 12 and 14 are only by way of example for the quantitation of the selected enzyme in an exemplary fluid sample in the presence of a selected coenzyme and the necessary substrate. The aforementioned connection of the tubes 10, 12 and 14 is such that the substrate-coenzyme solution flowing in tube 12 is segmented by segments of air supplied by tube 10, and the segmented solution in turn segments the sample stream added thereto. The sample supplied to the tube 14 may be one of a series of such samples supplied from a sampler such as that described in deJong U.S. Pat. No. 3,134,263, and wherein the samples are isolated one from another in flow along a conduit from the sampler by at least one segment of a gas. The volume of each untreated sample may be relatively small, on the order of 0.01 ml. The resultant stream flowing in tube 12 is transported through a mixing coil 20 interposed in tube 12. The outlet end of the tube 12 is coupled to an electrode assembly, indicated generally at 22, of a potentiostat. The pump tube 16 has an inlet end for supply of an electrolyte solution, such as saline, which serves as the salt bridge for the reference electrode.

Figure 2:
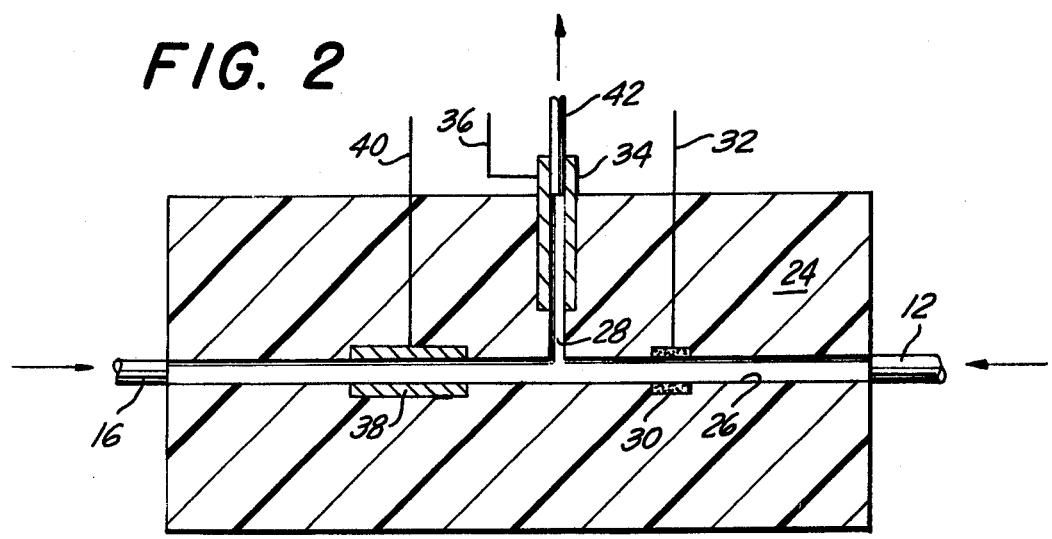
FIG. 2 is an enlarged, sectional view of the electrode assembly of FIG. 1.

As best shown in FIG. 2, the assembly 22 comprises a body 24 formed of electrical insulating material which may be inert plastic and having a bore 26 therethrough. The outlet ends of the pump tubes 12 and 16 are coupled to the respective ends of the bore 26 in the manner shown. A bore 28 intersects the bore 26 at right angles thereto and extends through one side of the body 24, as shown. A tubular indicator electrode 30 is interposed in the bore 26 so as to be flush therewith and may be constructed of glassy carbon or boron carbide so that hydrogen and oxygen overvoltages will not interfere with the coulometric measurements. One-hundred percent current efficiency is required for coulometric precision. The indicator electrode 30 is supplied with a lead 32. A tubular auxiliary electrode 34 is received in flush relation in the bore 28. The auxiliary electrode 34 may be formed of platinum and is provided with a lead 36. It will be noted that the indicator electrode 30 is interposed in the bore 26 to one side of the intersection of the bore 28 with the bore 26. At the other side of such intersection, a tubular reference electrode 38 is received in the bore 26 in flush relation therewith. It is the last-mentioned side of said intersection to which the electrolyte flow into tube 16. The reference electrode 38 may be formed of silver/silver chloride and is provided with a lead 40. As previously indicated, the electrode assembly 22 has two fluid inlets through the bore 26 and a common outlet through the bore 28 which is coupled to the inlet end of a tube 42 either directed to waste or through any required nonillustrated intermediate fluid supply conduits to another nonillustrated electrode assembly, similar to the assembly 22, for a different test on the same sample in which the NAD, formed by the action of the above inputted fluid substances, is now the coenzyme form for such test.

Figure 3:
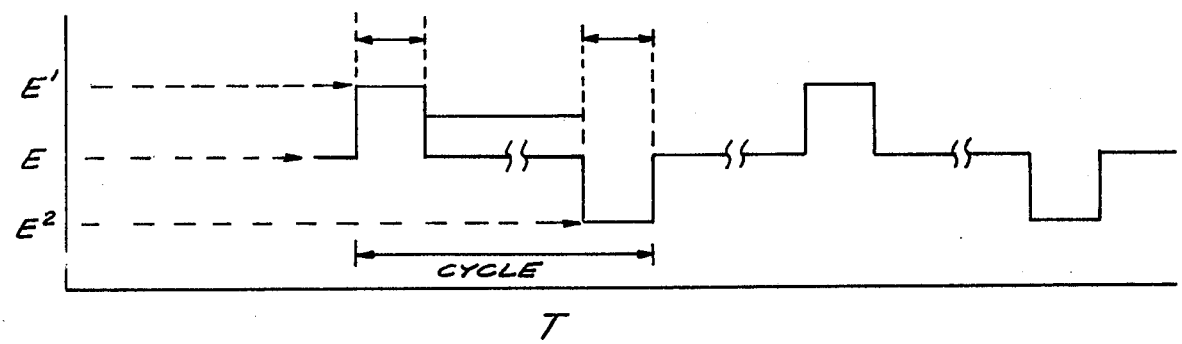
FIG. 3 is a diagram of a typical voltage pulse program for input to the auxiliary electrode of the apparatus.

As shown in FIG. 1, there is provided a voltage programmer 44 which provides voltage pulses of the desired shape and frequency. The voltage program may be that indicated by way of example in FIG. 3 wherein E represents the rest potential, $E^1$ represents in this example a voltage of approximately +0.7 and $E^2$ represents a voltage of approximately −1.2. As shown in FIG. 3, the pulse form may be rectangular, with T indicating time. The voltage is pulsed from E to $E^1$ where it may be maintained for one millisecond, for example, before returning to the rest potential E. Thereafter, the voltage is pulsed from E to $E^2$ where it may remain for the same time duration before returning to E. The interval between the end of the pulse $E^1$ and the beginning of the pulse $E^2$ may be approximately 1 second, for example, so that the pulses $E^1$ and $E^2$ are for purposes of measurement, essentially simultaneous. As shown, voltage pulses $E^1$ and $E^2$ alternate from the rest potential and a pair of such alternate pulses constitutes a cycle. These pulses are applied to the auxiliary electrode 34 during the reaction catalyzed by the enzyme in the presence of the coenzyme.

Figure 4:
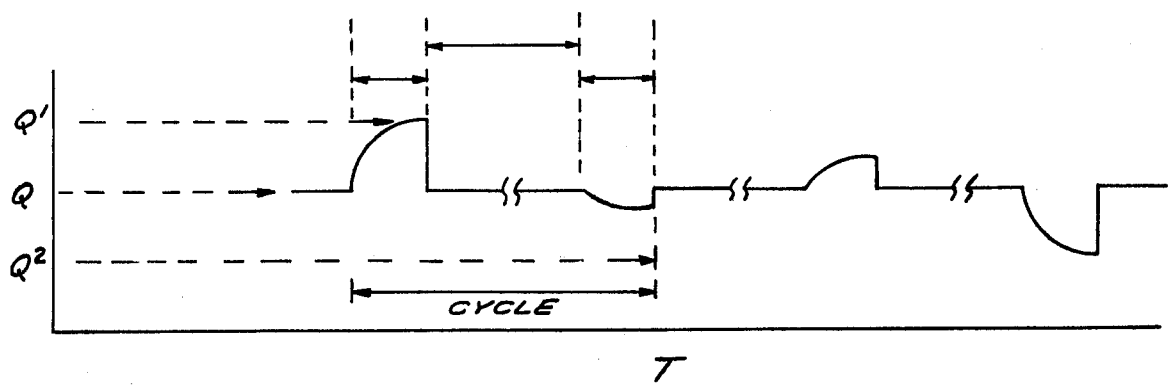
FIG. 4 is a diagram illustrating the coulometric responses at the indicator electrode.

FIG. 4 illustrates the coulometric responses $Q^1$, $Q^2$ from the baseline Q resulting from pulses $E^1$, $E^2$, respectively, which are amplitude dependent on the presence during the enzymatic reaction of NADH and NAD, respectively, with T indicating time. Hence, the amplitude of $Q^1$ represents at the time of each such response the remaining NADH. The increase in NAD is indicated over a period of time by the increase in the amplitude of each $Q^2$ response. The conversion of the coenzyme from the reduced form to the oxidized form over this time span, represented by each $Q^1$ and $Q^2$ response, indirectly indicates the activity level of the enzyme, LDH in this case, by current pulses passing to the indicator electrode 30 and along lead 32. The aforementioned voltage pulses $E^1$, $E^2$ of FIG. 3, respectively, do not interfere with the rate of the enzymatic reaction inasmuch as the pulses $E^1$ and $E^2$ represent only relatively small voltage changes which are of relatively short duration as previous indicated. Further, the enzymatic reaction in the sample in the bore 26 may be detected by the indicator electrode 30 statically, if desired. It is believed that such sampling of an enzyme reaction is permitted because such enzyme reactions are rate limited rather than mass-transport limited and because the indicator electrode 30 is only influenced by the chemistry of the reaction layer believed to be only 100 A thick.

The voltage programmer 44 has an output through lead 46 to a logic circuit 48 for timing and shaping the voltage pulses $E^1$, $E^2$. It is to be understood that the values of E, $E^1$ and $E^2$ may vary, depending on the particular analysis for which the apparatus of FIG. 1 is employed. The circuit 48 has an output along lead 50 to the potentiostat 52 which is connected by the aforementioned leads 36 and 40 to the aforementioned electrodes 34 and 38, respectively, of the assembly 22. The indicator electrode 30 of that assembly is connected along aforementioned lead 32 to a current/voltage converter 53 having an input thereto along lead 54 from a logic circuit 56 having a sample-and-hold function and a reset function. The circuit 56 has an input thereto along lead 58 from the circuit 48. An integrator 60 is provided receiving an input from the circuit 56 along lead 62 and an input along lead 64 from the current/voltage converter 53. The converter 53 may have an output along lead 68 to a nonillustrated conventional recorder for display of the analytical results in the sample-and-hold mode or an oscilloscope may display responses of the indicator electrode 30 in the form shown in FIG. 4, from which the activity level of the enzyme may be conventionally calculated, in this case LDH. It is to be understood that the same analysis of the activity level of this same enzyme may be analyzed by the apparatus of FIG. 1 in the opposite direction of the chemical reaction wherein lactic acid and NAD are substituted for the pyruvic acid and NADH inputted through the tube 12. Moreover, if the level of the enzyme is known the analysis performed by the apparatus of FIG. 1 may be for quantitation of the substrate which is unknown in a sample, which analysis is characterized by the same conversion of a coenzyme from one form, say an oxidized form, to a different form, say the reduced form thereof.

As previously indicated the use of the apparatus of FIG. 1 is not limited to use of the enzyme LDH nor the NAD/NADH half-reaction, but may be employed with the NADP/NADPH which is a similar coenzyme of the pyridine group. Further, the riboflavin prostetic group coenzymes may be employed in similar analyses which include the half-reaction or electrode couples $FMN/FMNH_2$, $FAD/FADH_2$ and as well CoA and CoQ. The analysis technique applies to all enzyme catalyzed reactions which require the presence of coenzymes that are electro-active and electro-chemically irreversible. The principal of the technique also generally applies to molecules that undergo bond cleavage or bond formation subsequent to oxidation changes in a method of analysis involving the above listed coenzymes of the pyridine and the prostetic groups of compounds in which oxidation changes are accompanied by hydrogenation or dehydrogenation. The practice of the invention with respect to either an enzyme level or a substrate concentration gives improved sensitivity as well as rapid measurement. As previously indicated, the invention permits, after one such analysis with either the oxidation or the reduction of a coenzyme, the reuse of that coenzyme in a subsequent analysis of the same sample for a different constituent of interest, for example, as in an SGPT catalyzed reaction for measurement of an SGPT activity level. Further, improved reproducibility and stability are achieved as the reduction and oxidation potentials differ by approximstely 1.8 volts or better than 10 Kcal/Mole in free energy difference.

In the use of the apparatus of FIG. 1, the voltage pulse, i.e., $E^1$, may be further modulated with a low-amplitude periodic voltage signal, i.e., sinusoidal or square wave having a frequency, for examples of 100 Hz. In this event, the duration of the pulse $E^1$ can be extended, for example, to one second whereby a modulation having amplitude of above and below that of $E^1$ are applied to the system. In effect, the auxiliary electrode is biased to a voltage $E^1$ at which one of the coenzyme forms is to be measured and modulation by the low-amplitude voltage signals forces a reaction at the indicator electrode. The bias voltage is selected such as to supply sufficient energy to the electrode and into the system to support the particular electro-chemical process, i.e., reduction or oxidation. The modulation, therefore, forces the reaction to occur alternately in the oxidation and reduction directions which can be measured. Also, the direction of the reaction can be controlled by any equivalent form of energy, e.g., heat, pressure, introduced into the system when the particular electrochemical process is supported. The signal processor 60, as before monitors the periodic current developed by the modulated voltage signals at indicator electrode 30, so as to measure NADH and an intermediate form during the oxidation process. This is the same mechanism that occurs in the first-described operation of the voltage programmer 44 wherein the system was biased to voltage $E^1$. However, in the usage of the programmer 44 presently being discussed, because additional energy is being supplied to the system in a rapidly modulated form, the coenzyme form and its reaction intermediate responds to the modulation voltage. This procedure allows added specificity to the measurement of the NADH, inasmuch as interference reactions in such system cannot follow the high perturbation frequency since most electrode interference reactions occur at a slower rate. It is evident that the NAD and its intermediate may be similarly measured by modulating to the voltage $E^2$. In other words, the present invention contemplates biasing the system at various voltage levels during the oxidation and reduction processes corresponding to particular coenzyme reactions, which may proceed concurrently with one or more of the enzyme reactions, and applying varying voltage signals to modulate any such bias and allow measurement of a particular coenzyme form and its intermediate. The repetition rate and amplitude of excursions of such varying signals should be such as not to interfere with any of the other ongoing reactions.

While one form of the apparatus and method for coulometric analysis of liquid samples has been illustrated and described, it will be apparent especially to those versed in the art, that the invention may take other forms and is susceptible to various changes in details without departure from the principles of the invention.

What is claimed is:

1. A method for determining the activity of an enzyme in a liquid sample treated with a coenzyme and a substrate for a reaction involving a change in the coenzyme from a first form to a second form, utilizing a three-electrode potentiostat including an auxiliary electrode, comprising the steps of: electro-sensitively contacting said treated sample simultaneously with the electrodes of said potentiostat, applying a voltage to said auxiliary electrode to support said reaction, modulating said voltage to change said coenzyme alternately between said first and second forms, and measuring at least one of said forms during said reaction.

2. A method as defined in claim 1, wherein: said measuring step includes measuring said first and second coenzyme forms concurrently.

3. A method as defined in claim 1, wherein: one of said first and second forms is an intermediate form of said coenzyme, and said biasing step and modulating step are cooperative to change said coenzyme periodically to said intermediate form.

4. A method for determining the activity of an enzyme in a liquid sample treated with a coenzyme and a substrate for a reaction involving a change in the coenzyme from a first form to a second form, utilizing a three-electrode potentiostat including an auxiliary electrode, comprising the steps of: electrosensitively contacting said treated sample simultaneously with the electrodes of said potentiostat, pulsing said auxiliary electrode over a period of time with voltage pulses so as to be biased above and below a baseline voltage, and measuring over a period of time the depletion of said first coenzyme form during said reaction.

5. A method as defined in claim 4, wherein: said pulsing of said auxiliary electrode comprises applying alternate different voltage pulses, said measuring step comprising measuring essentially simultaneously both of said coenzyme forms.

6. A method as defined in claim 5, wherein: said alternate different voltage pulsing is in opposite directions from said baseline.

7. A method as defined in claim 6, wherein: said voltage pulsing in one direction from said baseline is of approximately +0.7 volt and said voltage pulsing in the opposite direction from said baseline is of approximately −1.2 volts.

8. A method as defined in claim 4, wherein: said coenzyme is selected from the pyridine group.

9. A method as defined in claim 4, wherein: said coenzyme is selected from the flavin prostetic group.

10. A method as defined in claim 4, wherein: said sample is a blood sample.

11. A method for determining the concentration of a substrate in a liquid sample treated with an enzyme and a coenzyme for a reaction involving a change in the coenzyme from a first form to a second form, utilizing a three-electrode potentiostat including an auxiliary electrode, comprising the steps of: electrosensitively contacting said treated sample with the electrodes of said potentiostat simultaneously, applying a first voltage to said auxiliary electrode over a period of time to change said coenzyme to said second form, applying a modulating voltage to said first voltage, so as to eliminate interference by other reactants during measurement of said second form, and measuring over a period of time said second form.

* * * * *